(12) United States Patent
Lambie et al.

(10) Patent No.: US 6,200,586 B1
(45) Date of Patent: *Mar. 13, 2001

(54) BIOCIDAL AND AGROCHEMICAL SUSPENSIONS

(75) Inventors: Alan James Lambie, Kidderminster; Brian John Akred, Whitehaven; William John Nicholson, Halesowen; Jill Elizabeth Newton, Wordstey, all of (GB)

(73) Assignee: Albright & Wilson Limited, West Midlands (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/850,648

(22) Filed: May 2, 1997

Related U.S. Application Data

(63) Continuation of application No. 08/693,581, filed on Aug. 1, 1996, now abandoned, which is a continuation of application No. 08/446,042, filed on May 19, 1995, now abandoned, which is a continuation of application No. 08/345,007, filed on Nov. 23, 1994, now abandoned, which is a continuation of application No. 08/183,226, filed on Jan. 18, 1994, now abandoned, which is a continuation of application No. 08/045,909, filed on Apr. 12, 1993, now abandoned, which is a continuation of application No. 07/737,589, filed on Jul. 25, 1991, now abandoned, which is a continuation of application No. 07/491,298, filed on Mar. 9, 1990, now abandoned.

(30) Foreign Application Priority Data

Mar. 17, 1989 (DE) .................................................. 8906234

(51) Int. Cl.⁷ .................................................. A01N 25/04

(52) U.S. Cl. .......................... 424/417; 424/405; 424/408; 424/409; 424/490; 574/937; 504/116

(58) Field of Search ...................................... 424/405, 406, 424/408, 409, 417, 489, 490, 450; 571/937; 504/116

(56) References Cited

U.S. PATENT DOCUMENTS

| | | |
|---|---|---|
| 4,515,704 | 5/1985 | Akred et al. . |
| 4,618,446 | 10/1986 | Haslop et al. . |
| 4,659,497 | 4/1987 | Akred et al. . |
| 4,666,747 * | 5/1987 | Quinn ................................... 424/421 |
| 4,793,943 | 12/1988 | Haslop et al. . |
| 4,855,090 * | 8/1989 | Wallach ................................ 264/4.1 |
| 4,871,467 | 10/1989 | Akred et al. . |
| 4,897,308 | 1/1990 | Vanderberghe et al. .......... 428/402.2 |
| 4,911,928 * | 3/1990 | Wallach ................................ 424/450 |
| 5,019,392 * | 5/1991 | Wallach ................................ 424/420 |
| 5,023,086 * | 6/1991 | Wallach ................................ 429/450 |
| 5,037,653 * | 8/1991 | Dawson ................................ 424/405 |
| 5,160,530 * | 11/1992 | Misselbrook et al. .................. 71/121 |
| 5,198,353 | 3/1993 | Hawkins et al. . |

FOREIGN PATENT DOCUMENTS

| | | |
|---|---|---|
| 0 131 762 | 1/1985 | (EP) . |
| 0 253 682 | 1/1988 | (EP) . |
| 0 317 260 | 5/1989 | (EP) . |
| 2 123 846 | 2/1984 | (GB) . |
| 2 153 380 | 8/1985 | (GB) . |

* cited by examiner

Primary Examiner—Neil S. Levy
(74) Attorney, Agent, or Firm—Frishauf, Holtz, Goodman, Langer & Chick, P.C.

(57) ABSTRACT

A suspension comprising an aqueous structured surfactant having suspended therein particles or droplets of a substantially water insoluble or sparingly soluble biocidal or agrochemical active substance in a weight ratio of total surfactant to said active substance of less than 20:1.

11 Claims, No Drawings

BIOCIDAL AND AGROCHEMICAL SUSPENSIONS

This application is a Continuation of application Ser. No. 08/693,581, filed Aug. 1, 1996 ABD., which is a continuation application of Ser. No. 08/446,042, filed May 19, 1995 ABD., which is a continuation of application Ser. No. 08/345,007, filed Nov. 23, 1994 (abandoned), which is a continuation of Ser. No. 08/183,226, filed Jan. 18, 1994 (abandoned), which is a continuation of Ser. No. 08/045,909, filed Apr. 12, 1993 (abandoned), which is a continuation of application Ser. No. 07/737,589, filed Jul. 25, 1991 (abandoned), which is a continuation of application Ser. No. 07/491,298, filed Mar. 9, 1990 (abandoned).

The present invention provides a novel means of suspending relatively water-insoluble biocidal or agrochemical active substances in aqueous media without the need to employ environmentally harmful solvents. The term "agrochemical" is used herein broadly to cover chemicals that kill, entrap, repel or inhibit the growth or reproduction of unwanted organisms ("pests") or which protect or promote the healthy growth or reproduction of wanted organisms such as crops, ornamental plants, livestock and domestic animals, and which are useful in agriculture, horticulture, forestry, animal husbandry, agriculture, water treatment and land management, e.g. for application to fields, crops, orchards, livestock, gardens, woodland, hedgerows, parks, industrial estates, construction sites, airports, roads, railways, rivers, lakes, ponds, canals, irrigation and drainage works and the like.

Pests include vertebrate vermine such as rodents, rabbits and pigeons, invertebrates such as insects, mites, slugs, snails, nematodes, flatworms, millipedes and pathogenic protozoa, weeds, fungi, moulds, bryophites, lichens, algae, yeasts, bacteria and viruses.

"Biocidal and agrochemical active substances" include substances intended to kill, entrap, repel or to prevent or inhibit the growth or reproduction of any or all of the aforesaid pests. They also include growth promoters such as hormones, auxins, giberellins, nutrients, trace elements for application to soil or crops and biocides for use in water treatment such as boiler water, process water, cooling water, oil field injection water, central heating and air conditioning systems, but excludes animal foodstuffs and veterinary preparations for internal administration.

A number of substantially water insoluble biocidal and agrochemical active substances, are used extensively for controlling pests and/or for promoting the healthy growth of crops and livestock. For this purpose it is usually necessary or preferred to apply them in a fluid and preferably a diluted form. This frequently requires that the active substances be formulated in a stable aqueous based concentrate suitable for dilution with water.

Hitherto the only practical approach to formulating many of the less water soluble agrochemicals has been to dissolve them in an organic water-immiscible solvent usually an aromatic hydrocarbon such as xylene or isophorone and emulsify the resulting organic solution in water. A major disadvantage of this method is that the solvents commonly used are undesirable ecologically and from the stand point of human safety. Only the lack of a practicable alternative means of formulating many agrochemicals has prevented more severe restrictions on the use of such solvents.

Other approaches to the problem of applying some of the less water soluble agrochemicals have included the formulation of wettable powders or dispersible granules, both of which present problems for the user of handling solids and dispensing them in liquid. Attempts have been made to prepare concentrated aqueous suspensions of agrochemicals, but these have generally suffered from poor stability leading to sedimentation on standing, high viscosity leading to difficulties in handling and diluting, and/or high cost due to the use of expensive dispersants and thickeners. We have now found a method of suspending relatively water-insoluble biocides and agrochemicals to form highly concentrated, stable, pourable, aqueous-based suspensions suitable for dilution with water prior to application, which method does not rely on the use of potentiafly harmful solvents. The invention is generally applicable to the preparation of stable suspensions of a wide range of insoluble or sparingly-soluble biocides and agrochemicals, including many that have hitherto only been available in organic solvents, or as wettable powders, or dispersible granules, or as unstable suspensions.

We have discovered that substantially water-insoluble or sparingly soluble biocides and agrochemicals may be suspended in concentrations of 10 to 70% by weight or higher in aqueous structured surfactant systems. The expression "structured surfactant system" refers to aqueous systems in which surfactants form mesophases comprising structures larger than conventional spherical micelles, which interact to confer thixotropic properties on the aqueous medium. The structures may be solid, mesophase or liquid and may be in the form of multi layered spherulites or lamellae discontinuously dispersed or emulsified in the system or forming weak reticular structures or of rods or discs. The size of the structures may typically lie within the range 0.01 to 200 microns, preferably 0.5 to 20 microns. Structured surfactant systems are usually formed by the interaction of surfactants with dissolved electrolyte salts or bases. Such systems are present in some liquid detergents and cleaning compositions and have been described, for instance, in GB-2,123,846 and GB-A-2,153,380.

Use of structured surfactants to suspend agrochemicals offers a number of potential advantages. In many instances the activity and/or selectivity of the active material is increased. The structured surfactants are capable of suspending a wide range of particle sizes and may be adapted to a wide range of pH e.g. by appropriate choice of surfactant. The systems are generally obtainable in a shear stable form which facilitates wet milling.

Our invention provides a suspension comprising an aqueous structured surfactant having suspended therein particles or droplets of a substantially water insoluble or sparingly soluble biocidal or agrochemical active substance in a weight ratio of total surfactant to said active substance of less than 20:1. In particular our invention provides such suspensions which comprise water, sufficient surfactant to be able to provide a solid-suspending structure and sufficient dissolved surfactant-desolubilising electrolyte to form said structure.

Preferably the product may be a lamellar structure such as those described in GB-2 123 846 or most preferably a spherulitic structure such as those described in GB-A-2 153 380.

Surfactants

The compositions of our invention preferably contain at least 3%, more usually at least 4%, e.g. at least 5% by weight of surfactants. The surfactants may constitute up to about 35% by weight of the composition, although we prefer on economic grounds to use lower concentrations e.g. less than 30%, more usually less than 20%, preferably less than 15%, e.g. 7 to 10% by weight.

The surfactant may for example consist substantially of an at least sparingly water-soluble salt of sulphonic or mono esterified sulphuric acids e.g. an alkylbenzene sulphonate, alkyl sulphate, alkyl ether sulphate, olefin sulphonate, alkane sulphonate, alkylphenol sulphate, alkylphenol ether sulphate, alkylethanolamide sulphate, alkylethanolamide ether sulphate, or alpha sulpho fatty acid or its Easters each having at least one alkyl or alkenyl group with from 8 to 22, more usually 10 to 20, aliphatic carbon atoms. Said alkyl or alkenyl groups are preferably straight chain primary groups but may optionally be secondary, or branched chain groups. The expression "ether" hereinbefore refers to oxyalkylene and homo- and mixed polyoxyalkylene groups such as polyoxyethylene, polyoxypropylene, glyceryl and mixed polyoxyethylene-oxypropylene or mixed glyceryl-oxyethylene, glyceryl-oxypropylene groups, or glyceryl-oxyethylene-oxypropylene groups, typically containing from 1 to 20 oxyalkylene groups. For example, the sulphonated or sulphated surfactant may be sodium dodecyl benzene sulphonate, potassium hexadecyl benzene sulphonate, sodium dodecyl dimethyl benzene sulphonate, sodium lauryl sulphate, sodium tallow sulphate, potassium oleyl sulphate, ammonium lauryl monoethoxy sulphate, or monethanolamine cetyl 10 mole ethoxylate sulphate.

Other anionic surfactants useful according to the present invention include fatty alkyl sulphosuccinates, fatty alkyl ether sulphosuccinates, fatty alkyl sulphosuccinamates, fatty alkyl ether sulphosuccinamates, acyl sarcosinates, acyl taurides, isethionates, soaps such as stearates, palmitates, resinates, oleates, linoleates, rosins soaps and alkyl ether carboxylates and saponins. Anionic phosphate esters including naturally occurring surfactants such as lecithin may also be used. In each case the anionic surfactant typically contains at least one aliphatic hydrocarbon chain having from 8 to 22 preferably 10 to 20 usually an average of 12 to 18 carbon atoms, an ionisable acidic group such as a sulpho-, acid sulphate, carboxy, phosphono-or acid phosphate group, and, in the case of ethers, one or more glyceryl and/or from 1 to 20 ethyleneoxy and/or propyleneoxy groups.

Preferred anionic surfactants are sodium salts. Other salts of commercial interest include those of potassium, lithium, calcium, magnesium, ammonium, monoethanolamine, diethanolamine, triethanolamine and alkyl amines containing up to seven aliphatic carbon atoms.

The surfactant may optionally contain or consist of non-ionic surfactants. The nonionic surfactant may be e.g. a $C_{10-22}$ alkanolamide of a mono or di- lower alkanolamine, such as coconut or tallow monoethanolamide or diethanolamide. Other nonionic surfactants which may optionally be present, include ethoxylated alcohols, ethoxylated carboxylic acids, ethoxylated amines, ethoxylated alkylolamides, ethoxylated alkylphenols, ethoxylated glyceryl esters, ethoxylated sorbitan esters, ethoxylated phosphate esters, and the propoxylated, butoxylated and mixed ethoxy/propoxy and/or butoxy analogues of all the aforesaid ethoxylated ionionics, all having a $C_{8-22}$ alkyl or alkenyl group and up to 20 ethlyleneoxy and/or propyleneoxy and/or butyleneoxy groups, or any other nonionic surfactant which has hitherto been incorporated in powder or liquid detergent compositions e.g. amine oxides. The latter typically have at least one $C_{8-22}$, preferably $C_{10-20}$ alkyl or alkenyl group and up to two lower (e.g. $C_{1-4}$, preferably $C_{1-2}$) alkyl groups.

The preferred nonionics for our invention are for example those having an HLB range of 6–18 e.g. 8–12.

Our compositions may contain cationic surfactants, which include quaternary amines having at least one long chain (e.g. $C_{12-22}$ typically $C_{16-20}$) alkyl or alkenyl group optionally one benzyl group and the remainder of the four substituents short chain (e.g. $C_{1-4}$) alkyl groups. They also include imidazolines and quaternised imidazolines having at least one long chain alkyl or alkenyl group, and amido amines and quaternised amido amines having at least one long chain alkyl or alkenyl group. The quaternised surfactants are all usually salts of anions which impart a measure of water solubility such as formate, acetate, lactate, tartrate, chloride, methosulphate, ethosulphate, sulphate or nitrate.

Compositions of our invention may also contain one or more amphoteric surfactant, which include betaines, sulphobetaines and phosphobetaines formed by reacting a suitable tertiary nitrogen compound having a long chain alkyl or alkenyl group with the appropriate reagent, such as chloroacetic acid or propane sultone. Examples of suitable tertiary nitrogen containing compounds include: tertiary amines having one or two long chain alkyl or alkenyl groups and optionally a benzyl group, any other substituent being a short chain alkyl group; imidazolines having one or two long chain alkyl or alkenyl groups and amidoamines having one or two long chain alkyl or alkenyl groups.

The specific surfactant types described above are only exemplary of the commoner surfactants suitable for use according to the invention. Any surfactant capable of forming a structured system may be included. A fuller description of the principal types of surfactant which are commercially available is given in "Surface Active Agents and Detergents" by Schwartz Perry and Berch.

Electrolyte

Dissolved electrolyte compounds are strongly preferred constituents of our compositions. For the purposes of this Specification "electrolyte" means any water soluble, ionisable, non-surface-active compound which tends to desolubilise or "salt out" surfactants from solution or micellar solution. Although it is possible to prepare structured systems in the absence of electrolyte, if the surfactant concentration is sufficiently high, the mobility of such systems is often insufficient unless the surfactant has been selected with great care. Addition of electrolyte permits the preparation of mobile structured systems containing relatively low concentrations of surfactant.

The electrolyte may be present in concentrations up to saturation. Typically the less the amount of surfactant present, the more electrolyte will be required to form a structure capable of supporting solid materials. We generally prefer to use higher concentrations of electrolyte and lower concentrations of surfactant, and to select the cheapest electrolytes on economic grounds. Thus electrolyte should normally be present in a concentration of at least 1% by weight based on the total weight of the composition, more usually at least 2% e.g. more than 3% preferably more than 4% especially more than 5%. Usually the concentration is less than 30% more usually less than 20% e.g. less than 15% by weight. Typically the concentration is between 5 and 12%.

The maximum electrolyte concentration depends, among other things, on the type of structure, and the viscosity required as well as considerations of cost. We prefer to form spherulitic systems as described in our application GB-A-2,153,380 in order to obtain a satisfactory balance between mobility and high payload of suspended agrochemicals. The optimum concentration of electrolyte for any particular type and amount of surfactant may be ascertained as described in our aforesaid application by observing the variation of electrical conductivity with increasing electrolyte concentration until the first conductivity minimum is observed. Samples may be prepared and tested by centrifuging for 90 minutes at 20,000 G, adjusting the electrolyte concentration to obtain a suspending medium which does not separate into two phases in the centrifuge. Preferably the electrolyte concentration is adjusted to provide a composition which is non-sedimenting on standing for three months at ambient temperature, or at 0° C. or 40° C. Preferably also the electrolyte content is adjusted to provide a shear stable composition and, desirably, one which does not increase viscosity substantially after exposure to normal shearing.

Alternatively sufficient electrolyte may be added to form a lamellar system as described in GB-2,123,846, e.g. by adding enough electrolyte to ensure that the liquid suspending medium separates on centrifuging at 800 G for seventeen hours to form a lye phase containing little or no surfactant. The amount of water in the formulation may then be adjusted to obtain an optimum balance of mobility and stability.

In addition to cost, choice of electrolyte may depend on the intended use of the suspension. Fungicidal or pesticidal suspensions intended for crop protection preferably contain non-phytotoxic electrolytes, or concentrations insufficiently high to give rise to crop damage. Herbicidal compositions may contain auxiliary or synergistic herbicides as the electrolyte or part thereof. The selected electrolyte should also be chemically compatible with the solid to be suspended. Typical electrolytes for use in the present invention include alkali metal, alkaline earth metal, ammonium or amine salts including chlorides, bromides, iodides, fluorides, orthophosphates, condensed phosphates, phosphonates, sulphates, bicarbonate, carbonates, borates, nitrates, chlorates, chromates, formates, acetates, oxalates, citrates, lactates, tartrates, silicates, hypochlorites and, if required to adjust the pH, e.g. to improve the stability of the suspended solid or dispersed liquid or lower the phytotoxicity, acids or bases such as hydrochloric, sulphuric, phosphoric or acetic acids, or sodium, potassium, ammonium or calcium hydroxides, or alkaline silicates.

It may be convenient to select plant nutrients as, or as part of, the electrolyte e.g. nitrates, potash and/or phosphates. Electrolytes which form insoluble precipitates with the surfactants or which give rise to the formation of large crystals e.g. more than 1mm on standing are preferably avoided. Thus for example concentrations of sodium sulphate close to its saturation concentration in the composition at room temperature are undesirable.

Suspended Active Substance

The suspended biocidal or agrochemical active substance may comprise one or more agrochemicals or biocides such as selective or broad spectrum herbicides, defoliants, insecticides, miticides, moluscicides, nematicides and other vermicides, fungicides, bactericides, viricides and other pesticides, plant nutrients or growth or development regulators.

The particle or droplet size of the suspended material may vary widely. The maximum size that can be stably suspended depends upon the density of the suspended phase and the Yield Point of the suspending medium. However, for practical purposes we prefer that the maximum particle size is less than 1mm, preferably less than 500 microns. Most preferably the mean particle size and majority of the particles are in the range 0.1 to 250 microns e.g. 0.5 to 200 especially 1 to 100 microns. Often the mean particle size is between 1 and 10 microns.

Where the active substance is a low melting solid, it is sometimes desirable to incorporate a small amount of a melting point depressant to inhibit phase changes during manufacture or storage of the composition. Such changes may give rise to instability.

Examples of suitable active substances include ethofumesate, phenmedipham, dazomet, mancozeb, methylene bis thiocyanate, amitraz and triforine.

The proportion of the suspended phase can vary widely between about 1% by weight and about 80% by weight but most commonly lies between 10 and 60%. In general it is preferred on economic grounds to suspend as much agrochemical as can be accomodated without loss of mobility, eg 30 to 50%. The viscosity of the suspensions at 21 sec$^{-1}$ shear is typically between 0.2 and 50 Pascal seconds e.g. 0.2 to 5 Pascal seconds, preferably 0.2 to 3 Pascal seconds, especially 0.2 to 1.5 Pascal seconds. In general we prefer that the viscosity of the suspension measured at 136 sec$^{-1}$ should be in the range of 0.05 to 10 Pascal seconds, preferably 0.08 to 5 Pascal seconds e.g. 0.1 to 2 Pascal seconds most preferably 0.15 to 1 Pascal seconds.

Crystal Growth and Stability

One problem which arises with many suspensions of biocidal or agrochemical active substances in water is lack of stability due to interaction between the suspended agrochemical and the aqueous medium and/or other components of the formulation. For instance suspensions of amitraz present severe problems of crystal growth, arising from its slight solubility in the aqueous medium, while many pairs of agrochemicals which act synergistically or complementarily when applied to crops are chemically incompatible when stored together in aqueous concentrates.

The present invention provides according to a preferred embodiment a method of protecting agrochemicals suspended in an aqueous based formulation against interaction with the aqueous suspending medium or with other components of the formulation. We have discovered that agrochemicals encapsulated in water soluble encapsulants such as water soluble film-forming polymers, may be stably suspended in aqueous structured liquids and, surprisingly, retain their activity to a substantial degree on storage.

Encapsulation in water soluble film forming polymers and gums is a well known technique for binding a wide variety of sensitive ingredients, including pharmaceuticals and enzymes, and protecting them from deterioration during storage in air. Such capsules are conventionally used in an aqueous medium, which dissolves the capsule and releases the active ingredient immediately prior to use. It is not, therefore, on the face of it, possible to use such capsules to afford protection on storage in aqueous media.

We believe that the surprising stability of water soluble capsules in structured liquids is due to the relatively high electrolyte content of the latter. Electrolyte is required to interact with surfactants, which usually form a spherulitic or lamellar structure capable of suspending insoluble particles.

The suspending properties of a structured liquid detergent assist in preventing the protected agrochemical from undergoing agglomeration and sedimentation. We believe the electrolyte also prevents the dissolution of the water soluble capsules. The latter protect the agrochemicals until the formulation is diluted for use, when the electrolyte is diluted sufficiently for the capsule to dissolve and release the agrochemical.

According to one embodiment our invention provides an aqueous based agrochemical formulation comprising an aqueous suspending medium having suspended therein particles or droplets of a biocidal or agrochemical active substance encapsulated in or coacervated with a water soluble encapsulant which is insoluble in said aqueous suspending medium. Preferably the aqueous suspending medium comprises a surfactant and sufficient electrolyte to form the surfactant into a structure capable of supporting suspended solid particles and preventing dissolution of the encapsulant.

Where the encapsulant is solid at normal ambient temperatures or can be absorbed in solid granules, the encapsulated agrochemical may be formed for example by granulation or prilling. Granules of agrochemical in a fluid bed or pan granulator may be coated with molten encapsulant or with a concentrated aqueous solution of the encapsulant which is evaporated to leave an encapsulating film. Alternatively fine particles of agrochemical dispersed in molten or aqueous encapsulant may be prilled or spray dried, respectively, to form fine, encapsulated particles. Such technology is already well known. One disadvantage of coating or prilling, however, is that difficulties are sometimes encountered obtaining perfect encapsulation. Any interruption in the integrity of the coating can cause coated agrochemical granules to deteriorate rapidly when added to aqueous suspending media.

According to a preferred embodiment our invention provides a method of encapsulating or coacervating agrochemicals suspended in an aqueous structured surfactant, containing dissolved electrolyte, which comprises adding an aqueous solution of encapsulant thereto. The agrochemical and the encapsulant may be added together to the aqueous surfactant either before, after or simultaneously with the electrolyte.

The water soluble encapsulant for use according to our invention may be a water soluble film-forming organic macromolecule such as a polymer or gum. We particularly prefer a water soluble polyvinyl pyrrolidone. We can also use a polyvinyl alcohol, a cellulose derivative such as carboxymethyl cellulose, methyl cellulose, or hydroxypropylcellulose, a gum such as guar gum, gum benzoin, gum tragacanth, gum arabic or gum acacia, a protein such as casein, gelatin or albumin, a carbohydrate such as starch, dextrose, galactose, or amylose, an amylopectin, or polycarboxylates such as polyacrylates or polymaleates. The encapsulant is preferably not a surfactant or poly glycol.

The water soluble encapsulant is preferably a water soluble polymer that is precipitated by electrolyte, to form a solid gelatinous or viscous film or coherent layer surrounding the agrochemical particles. The solution of the encapsulant may conveniently have a concentration of from 0.5% by weight of encapsulant based on the weight of the solution up to saturation.

Where a polymer such as, for example, polyvinyl pyrrolidone is used as the encapsulant we prefer to use a polymer with a molecular weight of from 10,000 to 1,500,000 e.g. 15,000 to 1,000,000 more preferably 20,000 to 900,000, especially 25,000 to 800,000. In the case of polyvinyl alcohol we particularly prefer polymers with a molecular weight of 18,000 to 140,000 preferably 50,000 to 120,000 e.g. 80,000 to 100,000. Preferably any polyvinylalcohol used according to our invention is a partially hydrolysed polyvinyl ester of a lower (e.g. $C_{1 \; to \; 4}$) carboxylic acid, especially polyvinyl acetate, which has a degree of hydrolysis of greater than 25%, and desirably less than 95% especially 50 to 90% more preferably 60 to 80% e.g. 70 to 75%.

It is also possible to encapsulate particles of agrochemicals in hydrophobic liquids such as silicone oil, petroleum jelly or petroleum bright stock which are insoluble in aqueous surfactant. Such hydrophobic encapsulants may be preferred for certain pesticides whose retention and activity on leaves may be enhanced by the presence of hydrophobic liquid medium.

Solid or liquid agrochemicals may be dispersed in a hydrophobic liquid such as silicone oil and the dispersion itself dispersed in the aqueous surfactant medium.

The encapsulated agrochemical system preferably has a mean particle size in the range $2\mu$ to 2.5 mm especially $5\mu$ to 1 mm desirably $10\mu$ to $700\mu$, more desirably $100\mu$ to $500\mu$. We particularly prefer to disperse particles in the range 100 to $350\mu$.

The protected particles typically comprise from 0.5 to 90% by weight of encapsulant based on the weight of the particle, preferably 1 to 50% eg 2 to 20%.

Stability may also be affected by agglomeration or similar interaction between suspended crystallites. This may be avoided by use of steric inhibitors such as polyelectrolytes. For instance a minor proportion e.g. from 0.1 to 10% preferably 0.5 to 5% especially 1 to 4% by weight of a poly acrylate or maleic anhydride copolymer may be used.

Other Ingredients

We prefer that the suspensions of our invention should have low foaming properties. While this can be achieved by selecting inherently low foaming surfactants, we generally prefer to include antifoams such as silicone oil antifoams, phosphate esters, fatty alcohols or hydrocarbon oils. Typically the antifoam is required in concentrations of 0.1 to 5% by weight.

The composition may optionally include a suspending agent such as carboxymethyl cellulose or polyvinyl pyrrolidone, e.g. in amounts of from 0.1 to 5% preferably 0.5 to 2% by weight.

The composition may also, optionally, contain synergists, soluble biocides, plant nutrients, plant growth regulators, preservatives, buffers, antifreezes, colouring, and fragrances.

We prefer that the composition does not contain any organic solvents, either water miscible solvents such as lower mono or polyhydroxy alchols, ketones and polyethers or water-immiscible solvents such aromatic hydrocarbons, nor any hydrotropes such as urea, benzene sulphonate or lower alkyl benzene sulphonates. Solvents and hydrotropes tend to interfere with surfactant structuring and require the use of substantially increased amounts of surfactant and/or electrolyte. They also increase the cost of the formulation without generally increasing performance. Aromatic solvents are in addition undesirable on toxicity grounds. We therefore prefer, if present at all, that solvents and hydrotropes are each present in proportions less than 10%, more preferably less than 5%, most preferably less than 1%, e.g. less than 0.5%, usually less than 0.1% and most commonly less than 0.05% by weight.

We similarly prefer that polymeric thickening agents such as gums are absent or present in concentrations less than 5%, preferably less than 0.5% since they are not generally necessary to stabilise the compositions and since they increase the cost and viscosity of the suspensions.

The invention will be illustrated by the following examples in which all percentages are by weight based on total weight.

EXAMPLE 1

| | | |
|---|---|---|
| Coconut monoethanolamide | (C$_{12}$C$_{14}$) | 2.1% |
| Linear alkyl benzene sulphonate | (C$_{12}$) | 5.2% |
| Water | | 51.4% |
| Silicone defoamer | | 0.1% |
| Ethofumesate | | 40.0% |
| Sodium nitrate | | 1.2% |

EXAMPLE 2

| | | |
|---|---|---|
| Linear alkyl benzene sulphonate | (C$_{12}$) | 4.9% |
| Na lauryl 3 mole ethoxy sulphonate | | 1.7% |
| Water | | 49.7% |
| Silicone defoamer | | 0.1% |
| Ethofumesate | | 40% |
| Sodium nitrate | | 3.6% |

EXAMPLE 3

| | | |
|---|---|---|
| Coconut diethanolamide | (C$_{12}$C$_{14}$) | 3% |
| Linear alkyl benzene sulphonate | (C$_{12}$) | 3% |
| Water | | 50.9% |
| Silicone defoamer | | 0.1% |
| Sodium nitrate | | 3% |
| Ethofumesate | | 40% |

EXAMPLE 4

| | | |
|---|---|---|
| Coconut diethanolamide | (C$_{12}$C$_{14}$) | 3% |
| Linear alkyl benzene sulphonate | | 3% |
| Silicone defoamer | | 0.1% |
| Water | | 49.9% |
| Sodium polyacrylate (m.w 2,500) | | 1% |
| Sodium nitrate | | 3% |
| Ethofumesate | | 40% |

EXAMPLE 5

| | |
|---|---|
| Linear alkyl diethanolamide | 1.3% |
| Coconut diethanolamide | 5.0% |
| Na lauryl 3 mole ehtoxy sulphate | 0.4% |
| Na HCO$_3$ | 4.6% |
| Silicone defoamer | 0.1% |
| Atrazine | 30% |
| Water | 58.6% |

EXAMPLE 6

| | |
|---|---|
| Amitraz | 50% |
| 30% aqueous sodium C$_{10-14}$ linear alkylbenzene sulphonate | 8.1% |
| 70% aqueous sodium lauryl 3 mole ethoxy sulphate | 1.7% |
| polyvinyl pyrrolidone | 0.56% |
| Potassium carbonate | 4% |
| Silicone antifoam | 0.04% |
| Water | 35.6% |

The amritraz was milled to <5μ, in the presence of the aqueous surfactants. The polymer was added as 4% aqueous solution with stirring. Finally the carbonate was added as 40% aqueous solution with stirring.

All the Examples formed homogeneous mobile suspensions which dispersed readily in water to form sprayable dispersions of adequate stability.

The storage properties of Example 4 were particularly good, and substantially improved compared to Examples 1, 2 and 3.

The storage properties of Example 6 were excellent. In comparison, amitraz suspensions without PVP were unstable due to rapid crystal growth.

EXAMPLE 7

| | |
|---|---|
| Sodium linear $C_{12}$ alkyl benzene sulphonate | 5.33% |
| Sodium $C_{12-14}$ alkyl 3 mole ethoxy sulphate | 1.87% |
| Silicone antifoam | 0.1% |
| Sodium bicarbonate | 2.6% |
| 45% aqueous solution of polycarboxylic acid (MW 2,700) | 2.22% |
| Ethofumesate | 45% |
| Water | to 100% |

Rheology good
Stable for 3 months at R.T. and 50° C.
Thickening can occur after 3 F/T cycles
Good dispersability

EXAMPLE 8

| | |
|---|---|
| Sodium linear $C_{12}$ alkyl benzene sulphonate | 5.33% |
| Sodium $C_{12-14}$ alkyl 3 mole ethoxy sulphate | 1.87% |
| Silicone antifoam | 0.1% |
| Sodium bicarbonate | 2.6% |
| 45% aqueous solution of polycarboxylic acid (MW 2,700) | 2.22% |
| Triforine | 45% |
| Water | to 100% |

Rheology good
Stable for 3 months at R.T.
Thickening can occurs at 50° C.
Thickening can occur on F/T cycling
Good dispersability

EXAMPLE 9

| | |
|---|---|
| Isopropylamine linear $C_{12}$ alkyl benzene sulphonate | 6.3% |
| Silicone | 0.1% |
| Sodium bicarbonate | 6.4% |
| Poly vinyl alcohol | 1.0% |
| Phenmedipham | 20% |
| Water | to 100% | all characteristics good

EXAMPLE 10

| Sodium linear $C_{12}$ alkyl benzene sulphonate | 6.0% |
|---|---|
| Linear $C_{12-13}$ alcohol 3 mole ethoxylate | 6.0% |
| Sodium bisulphate | 4.8% |
| Phenmedipham | 20% |
| Water | to 100% | all characteristics good

EXAMPLE 11

| Nonyl phenyl ethoxylate | 4.2% |
|---|---|
| Isopropylamine linear $C_{12}$ alkyl benzene sulphonate | 3.9% |
| Silicone antifoam | 0.1% |
| Sodium bisulphate | 6.7% |
| Phenmedipham | 16% |
| Water | to 100% | all characteristics good

EXAMPLE 12

| Cononut diethanolamide | 2.6% |
|---|---|
| Sodium linear $C_{12}$ alkyl benzene sulphonate | 2.6% |
| Silicone antifoam | 0.1% |
| Sodium nitrate | 3.96% |
| Mancozeb | 1% |
| Water | to 100% |

Rheology good
thickens on storage at 50° C.

EXAMPLE 13

| Linear $C_{12}$ alcohol 3 mole ethoxylate | 3% |
|---|---|
| Sodium linear $C_{12}$ alkyl benzene sulphonate | 12% |
| Sodium dihydrogen phosphate | 2.5% |
| methylene bisthiocyanate | 30% |
| 45% aqueous solution of poly carboxylic acid (M 2,100) | 2.22% |
| Water | to 100% | all characteristics good

EXAMPLE 14

| Sodium linear $C_{12}$ alkyl benzene sulphonate | 8% |
|---|---|
| Linear $C_{12-13}$ alcohol 3 mole ethoxylate | 1% |
| Sodium tripolyphosphate | 4% |
| Dazomet | 25% |
| Water | to 100% |

What is claimed is:

1. A composition comprising:
   (a) a substantially water insoluble or sparingly soluble biocidally or agrochemically active substance having a mean particle size in the range of 0.5 to 200 microns and being selected from the group consisting of ethofumesate, phenmedipham, dazomet, mancozeb, methylene bis thiocyanate, amitraz, triforine and atrazine;
   (b) an aqueous structured surfactant system, comprising water and surfactant, and having a surfactant structure in the form of multilayered spherulites or lamellae; said spherulites or lamellae being discontinuously dispersed or emulsified in said aqueous phase or forming weak reticular structures therein; said structured surfactant system having interstices between said surfactant structures;
   (c) an aqueous continuous phase;
   (d) 1–30% by weight of a surfactant desolubilising electrolyte;
   said surfactant being present in an amount of 3–35% by weight and being selected from the group consisting of;
       anionic surfactants selected from the group consisting of:
           (i) at least sparingly water-soluble salts of sulphonic acids;
           (ii) at least sparingly water-soluble salts of mono esterified sulphuric acids;
           (iii) at least sparingly water-soluble salts of alpha-sulpho fatty acids or esters of said acids;
           (iv) fatty alkyl sulpho succinates or ether sulphosuccinates;
           (v) fatty alkyl sulphosuccinamates or ether sulphosuccinates;
           (vi) acyl taurides;
           (vii) isethionates; and
           (viii) soaps;
       non-ionic surfactants selected from the group consisting of:
           (i) $C_{10}$–$C_{22}$ alkanolamides of mono- or di-lower alkanolamines;
           (ii) ethoxylated alcohols, carboxylic acids or amines;
           (iii) ethoxylated alkylolamides or alkylphenols;
           (iv) ethoxylated glyceryl, sorbitan or phosphate esters;
           (v) propoxylated, butoxylated, mixed ethoxy-, propoxy- or butoxy analogues of (ii), (iii) and (iv); and
           (vi) amine oxides;
       cationic surfactants selected from the group consisting of:
           (i) quaternary amines;
           (ii) imidazolines or quaternised imidazolines;
           (iii) amido-amines; and
           (iv) quaternised amido-amines;
   and
       amphoteric surfactants selected from the group consisting of:
           (i) betaines;
           (ii) sulphobetaines; and
           (iii) phosphobetaines;
   said substantially water insoluble or sparingly soluble biocidally or agrochemically active substance being dispersed in and through said aqueous continuous phase (c) with a weight ratio of said surfactant to said active substance (a) of less than 20:1;
   said active substance (a) and said aqueous continuous phase (c) each occupying said interstices between said surfactant structures, whereby said active substance (a) is suspended by said structured surfactant system (b); and wherein said active substance (a) is present in said aqueous continuous phase (c), in a proportion of from 10% to 60% by weight of said composition.

2. A pourable, aqueous composition comprising:
   (a) a substantially water insoluble or sparing soluble particulate biocidally active or agriculturally active substance having a mean particle size in the range of 0.5 to 200 microns and being selected from the group consisting of ethofumesate, phenmedipham, dazomet, mancozeb, methylene bis thiocyanate, amitraz, triforine and atrazine;

(b) surfactant;

(c) an aqueous continuous phase; and (d) 1–30% by weight of a surfactant desolubilising electrolyte;

wherein said active substance (a) is present in a proportion of from 10% to 60% by weight based on the total weight of said aqueous composition, said surfactants (b) is present in a proportion of from 5% to 35% by weight based on the total weight of said aqueous composition, and being selected from the group consisting of:

anionic surfactants selected from the group consisting of:

(i) at least sparingly water-soluble salts of sulphonic acids;

(ii) at least sparingly water-soluble salts of mono esterified sulphuric acids;

(iii) at least sparingly water-soluble salts of alpha-sulpho fatty acids or esters of said acids;

(iv) fatty alkyl sulpho succinates or ether sulphosuccinates;

(v) fatty alkyl sulphosuccinamates or ether sulphosuccinamates;

(vi) acyl taurides;

(vii) isethionates; and (viii) soaps;

non-ionic surfactants selected from the group consisting of:

(i) $C_{10}$–$C_{22}$ alkanolamides of mono- or di-lower alkanolamines;

(ii) ethoxylated alcohols, carboxylic acids or amines;

(iii) ethoxylated alkylolamides or alkylphenols;

(iv) ethoxylated glyceryl, sorbitan or phosphate esters;

(v) propoxylated, butoxylated, mixed ethoxy-, propoxy- or butoxy analogues of (ii), (iii) and (iv); and (vi) amine oxides;

cationic surfactants selected from the group consisting of:

(i) quaternary amines;

(ii) imidazolines or quaternised imidazolines;

(iii) amido-amines; and (iv) quaternised amido-amines;

and amphoteric surfactants selected from the group consisting of:

(i) betaines;

(ii) sulphobetaines; and (iii) phosphobetaines;

said electrolyte (d) is present in a proportion sufficient to form, a solid suspending surfactant structure upon interaction with said surfactant (b), said solid suspending surfactant structure being an aqueous structured surfactant system, comprising water and the surfactant, and having a surfactant structure in the form of multilayered spherulites or lamellae; said spherulites or lamellae being discontinuously dispersed or emulsified in said aqueous phase or forming weak reticular structures therein; said structured surfactant system having interstices between said surfactant structures;

a proportion of said electrolyte may be dissolved in said aqueous continuous phase (c), and said active substance (a) is dispersed in said continuous medium (c) and suspended by said surfactant structures, said structures also being independently dispersed throughout said continuous medium (c).

3. The composition of claim 1, further comprising:

(a) a substantially water insoluble or sparingly soluble biocidal or agrochemical active substance;

(b) surfactant;

(c) an aqueous continuous phase; and (d) surfactant desolubilising electrolyte;

wherein said surfactant is present in a proportion sufficient to be able to provide a solid suspending surfactant structure, and said surfactant desolubilising electrolyte (d) is present in a proportion sufficient to be able to form solid suspending structures by interaction with said surfactant, and in which a proportion of said electrolyte (d) is dissolved in said continuous phase (c).

4. The composition of claim 1, wherein said structured surfactant system (b) comprises a lamellar system discontinuously dispersed or emulsified in the system.

5. The composition of claim 1, wherein said structured surfactant system (b) comprises a spherulitic structure.

6. A composition of claim 1, wherein said composition comprises from 5% to 35% by weight of surfactant.

7. The composition of claim 1 or 2 wherein said surfactant is selected from the group consisting of sodium alkylbenzane sulphonates, alkyl mono or di-ethanolamides, alkyl ether sulphates, ethoxylated alcohols and mixtures thereof.

8. The composition of claim 3 or 2 wherein said electrolyte (d) in said composition is present in a proportion of between 5% to 12% by weight, based on the total weight of said composition, of which a proportion may be dissolved in said continuous aqueous medium (c).

9. A composition of claim 1 or 2 wherein said active substance (a) is chosen from the group consisting of ethofumesate, phenmedipham, dazomet, mancozeb, methylene bis thiocyanaate, amitraz or triforine.

10. A composition of claim 1 or 2 wherein said active substance (a) is dispersed throughout said continuous aqueous medium (c), said active substance (a) being encapsulated in or concentrated with a water soluble encapsulant, said encapsulant being insoluble in said composition.

11. The composition of claim 3 comprising from 5% to 35% by weight surfactant.

* * * * *